United States Patent
Queisser et al.

(10) Patent No.: US 6,346,324 B1
(45) Date of Patent: *Feb. 12, 2002

(54) CIS-BRIDGED METAL COMPLEXES AND CATALYST SYSTEMS CONTAINING THE SAME

(75) Inventors: Joachim Queisser, Mannheim; Michael Slany, Kirchheim; Ansgar Schäfer, Karlsruhe; Michael Schulz, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/646,618

(22) PCT Filed: Apr. 1, 1999

(86) PCT No.: PCT/EP99/02282

§ 371 Date: Sep. 18, 2000

§ 102(e) Date: Sep. 18, 2000

(87) PCT Pub. No.: WO99/52917

PCT Pub. Date: Oct. 21, 1999

(30) Foreign Application Priority Data

Apr. 14, 1998 (DE) .......................... 198 16 190

(51) Int. Cl.[7] .......................... D02G 3/00; C08G 67/02
(52) U.S. Cl. .......................... 428/364; 528/392; 568/17; 524/701; 524/706; 524/709; 524/711; 524/712; 524/714; 524/742; 524/745; 502/152; 502/154; 502/158; 502/159; 502/162; 502/164; 502/168; 502/169
(58) Field of Search .......................... 528/392; 568/17; 524/701, 706, 709, 711, 712, 714, 742, 745; 502/152, 154, 158, 159, 162, 164, 168, 169; 428/364

(56) References Cited

U.S. PATENT DOCUMENTS 6,103,867 A 8/2000 Slany et al. ................. 528/392

FOREIGN PATENT DOCUMENTS

EP 0 121 965 10/1984

OTHER PUBLICATIONS

Drent et al. "Efficient Palladium Catalysts for the Copolymerization of Carbon Monoxide with Olefins to Produce Perfectly Alternating Polyketones" Journal of Organometallic Chemistry, No. 417 (1991) pp. 235–251.

Seringag et al. "Synthesis of Sulfonated Animomethylphosphines and Some Nickel(II), Palladium(II), Platinum(II) and Rhodium(I) Complexes" Transition Met. Chem. No. 20 vol. 6 (1995) pp. 548–561.

Primary Examiner—Samuel A. Acquah
(74) Attorney, Agent, or Firm—Keil Weinkauf

(57) ABSTRACT

Disclosed is a cis-bridged metal complex of the formula (I)

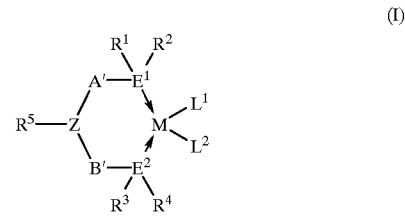

where $R^5$ is an electron-withdrawing radical, and catalyst systems based on these complexes for copolymerizing carbon monoxide and olefinically unsaturated compounds.

8 Claims, No Drawings

CIS-BRIDGED METAL COMPLEXES AND CATALYST SYSTEMS CONTAINING THE SAME

The present invention relates to cis-bridged metal complexes of the formula (I)

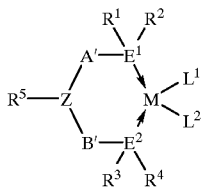

(I)

where:
- $R^5$ is an electron-withdrawing radical,
- M is a metal of group VIIIB of the periodic table of the elements,
- $E^1$, $E^2$ are each an element of group VA of the periodic table of the elements,
- z is nitrogen or phosphorus,
- $R^1$ to $R^4$ are substituents selected, independently of one another, from the group consisting of $C_1$–$C_{20}$-organocarbon and $C_3$–$C_{30}$-organosilicon radicals in substituted and unsubstituted form,
- A', B' are $C_1$–$C_4$-alkylene units in substituted or unsubstituted form, silylene-bridged organic radicals or $NR^6$ radicals,
- $R^6$ is hydrogen or a substituent selected from the group consisting of $C_1$–$C_{20}$-organocarbon and $C_3$–$C_{30}$-organosilicon radicals, and
- $L^1$,$L^2$ are formally charged ligands.

Furthermore, the present invention relates to a process for preparing such metal complexes and also to their use as essential constituents of catalyst systems for the copolymerization of carbon monoxide with olefinically unsaturated compounds.

In addition, the present invention relates to catalyst systems comprising, as active constituents, a) a cis-bridged metal complex of the formula (I) and b) one or more Lewis acids or protic acids or a mixture of Lewis acids and protic acids. The present invention also relates to processes for the preparation of copolymers of carbon monoxide and olefinically unsaturated monomer compounds and also to the use of catalyst systems based on cis-bridged metal complexes of the formula (I) for the preparation of copolymers of carbon monoxide and olefinically unsaturated monomer compounds. Finally, the invention relates to the use of the copolymers obtained according to the invention and also for the production of fibers, sheets, moldings and coatings said fibers, sheets, moldings and coatings.

Catalyst systems for the preparation of copolymers of carbon monoxide and olefinically unsaturated compounds are known. Active catalyst constituents used are generally cis-palladium complexes chelated by bidentate phosphine ligands such as $[Pd(R_2P(CH_2)_nPR_2)(OAc)_2]$ (cf. EP 0 121 965). Ligands which have been found to be particularly useful for the copolymerization of carbon monoxide with ethylene and/or propylene are bidentate phosphine ligands having a propylene bridge, with preference being given to using catalyst systems comprising, for example, [(dmppp)Pd(OAc)$_2$](BF$_4$)$_2$ as metal complex (dmppp=1,3-bis{di-(2-methoxyphenyl)phosphino}propane) (cf. J. Organomet. Chem. 417 (1991), 235 ff).

However, the preparation of suitable ligand systems such as 1,3-bis{di(2-methoxyphenyl)phosphino}propane) or 1,3-bis{diphenylphosphino}propane (dppp) requires the handling of extremely reactive and also extremely flammable and toxic compounds. The preparation of, for example, alkylene-bridged phosphine ligands therefore usually requires high investment in terms of equipment. In particular, an industrial-scale preparation is not unproblematical for safety reasons. Furthermore, unsymmetrically substituted alkylene-bridged ligands, i.e. those having different phosphine substituents or containing different chelating atoms, are only obtainable to a limited extent from dibromo- or dichloro-terminated alkylene compounds. In addition, structural analogs of said chelating ligands, even those which differ only slightly from a known structure, are frequently not obtainable by the same or similar route but require a complicated, individual synthesis.

German Patent Applications 19651685.4 and 19651786.9 describe cis-bridged metal complexes or catalyst systems based on these complexes, respectively, which remedy the problems described above. In particular, the complexes used feature an amino or phosphino functionality integrated in the bidentate chelating ligands. These systems are also suitable for covalent linking to a support material.

The abovementioned systems have the disadvantage that it is not always possible to maintain a constant catalyst activity at extended reaction times, in particular when the copolymerization is carried out at elevated temperature.

It is an object of the present invention to provide metal complexes or catalyst systems which are based on these complexes for the copolymerization of carbon monoxide copolymers and which will have consistently high catalyst activity, even under prolonged polymerization times, without losing the advantages of nitrogen- or phosphorus-bridged ligand systems, and will provide good yields in a reproducible manner.

We have found that this object is achieved by the cis-bridged metal complexes defined at the beginning. We have also found a process for the preparation of these metal complexes and also the use of the metal complexes (I) defined as essential constituents of catalyst systems suitable for copolymerizing carbon monoxide and olefinically unsaturated compounds.

The invention also provides catalyst systems comprising, as active constituents, a) a cis-bridged metal complex of the formula (I) and b) one or more Lewis acids or protic acids or a mixture of Lewis acids and protic acids, processes for the preparation of copolymers of carbon monoxide and olefinically unsaturated monomer compounds and also the use of catalyst systems based on cis-bridged metal complexes for the preparation of copolymers of carbon monoxide and olefinically unsaturated monomer compounds. Furthermore, the invention provides the use of the copolymers obtained according to the invention for the preparation of fibers, sheets, moldings and coatings and also said fibers, sheets, moldings and coatings.

Suitable metals M in the metal complexes of the present invention are the metals of group VIIIB of the periodic table of the elements, i.e. iron, cobalt and particularly nickel, and especially the platinum metals such as ruthenium, rhodium, osmium, iridium and platinum and very particularly palladium. In the metal complexes, the metals can be present in formally uncharged, formally singly positively charged or preferably formally doubly positively charged form.

Suitable elements $E^1$ and $E^2$ in the chelating ligands $(R^1)(R^2)E^1$—A'—Z($R^5$)—B'—$E^2(R^3)(R^4)$ (II) of the metal complexes (I) of the invention are the elements of main group V of the periodic table of the elements (group VA), i.e. nitrogen, phosphorus, arsenic, antimony or bismuth. Particularly suitable elements are nitrogen or phosphorus, especially phosphorus. The chelating ligands in (II) can contain different elements $E^1$ and $E^2$; for example, it is possible for $E^1$ to be nitrogen and for $E^2$ to be phosphorus.

The bridging structural unit in the metal complexes of the invention is composed of the components A', B' and Z (see also formulae (I) and (II)). For the purposes of the present invention, the bridging structural unit is basically a multiatomic group which connects the elements $E^1$ and $E^2$ to one another.

The component Z used is either nitrogen or phosphorus, especially nitrogen.

The units A' and B' can be, in each case independently of one another, $C_1$–$C_4$ organocarbon or organosilicon radicals. Suitable organic radicals are $C_1$–$C_4$-alkylene units in substituted or unsubstituted form, for example methylene, ethylene, propylene, and also ethylidene, propylidene and benzylidene. Preference is given to using methylene, ethylene, ethylidene and benzylidene, particularly preferably methylene.

Furthermore, A' and B', likewise independently of one another, can be silylene radicals, for example —$R^a$—Si—$R^b$—, where $R^a$, $R^b$ are $C_1$–$C_4$-alkylene units in substituted or unsubstituted form, for example methylene, ethylene or ethylidene, arylene units, in particular o-phenylene, or aralkylidene units, in particular benzylidene, where the free valencies on the silicon may be saturated by alkyl groups such as methyl, isopropyl or t-butyl, aryl groups such as phenyl, or aralkyl groups such as benzyl.

A' and B' can also each be an —$NR^6$ unit where —$R^6$ is hydrogen or a substituent selected from the group consisting of $C_1$–$C_{20}$-organocarbon and $C_3$–$C_{30}$-organosilicon radicals such as $C_1$–$C_{10}$-alkyl, in particular methyl, ethyl, aryl, in particular phenyl, or aralkyl, in particular benzyl.

A' and B' can likewise be a monoatomic, diatomic, triatomic or tetraatomic constituent of an aliphatic or aromatic ring system. For example, A' and B' can each be a methylene or ethylene unit of a cyclopropyl, cyclopentyl or cyclohexyl ring. Other possible ring systems are aliphatic and aromatic heterocycles.

A' and B' can also each be a constituent of a heterocycle which is formed by the components A'—Z—$R^5$ or B'—Z—$R^5$, i.e. A'—Z—$R^5$ or B'—Z—$R^5$ can form a substituted or unsubstituted pyrrolidine or piperidine ring.

In the case of a monoatomic organocarbon bridge between the units Z and $E^1$ or $E^2$, A' and B' are each, independently of one another, preferably a —$CR^7R^8$ unit, $R^7$ and $R^8$, likewise independently of one another are hydrogen, $C_1$–$C_{10}$-alkyl such as methyl, ethyl or propyl, $C_6$–$C_{14}$-aryl, for example phenyl, $C_7$–$C_{20}$-aralkyl or heteroaryl, in particular hydrogen. The monoatomic bridge containing the radicals $R^7$ and $R^8$ can also form a ring system such as cyclopropyl, cyclopentyl or cyclohexyl. $R^7$ and $R_8$ are preferably hydrogen.

Suitable organocarbon radicals $R^1$ to $R^4$ are, independently of one another, for example, aliphatic and cycloaliphatic and also aromatic and heteroaromatic radicals having from 1 to 20 carbon atoms.

Suitable straight-chain aliphatic radicals include methyl, ethyl, propyl, butyl, pentyl, hexyl and octyl.

Suitable branched aliphatic radicals include $C_3$–$C_{20}$-alkyl radicals, preferably $C_3$–$C_{12}$-alkyl radicals such as isopropyl, isobutyl, s-butyl, neopentyl and t-butyl, also alkylaryl in each case having from 1 to 6 carbon atoms in the alkyl radical and 6 to 14 carbon atoms in the aryl radical.

Particularly suitable branched aliphatic radicals are t-butyl, isopropyl and s-butyl.

Alkyl groups having branching located further out are also well suited as substituents $R^1$ to $R^4$, for example isobutyl, 3-methylbut-2-yl and 4-methylpentyl.

Suitable cycloaliphatic radicals are, for example, $C_3$–$C_{10}$-monocycles such as cyclopropyl, cyclobutyl, cyclopentyl, cyclohexyl and menthyl and also bicyclic radicals such as norbornyl, pinanyl, bornyl and bicyclononyl with any linkage of the ring framework to the atoms $E^1$ and $E^2$. The cycloaliphatic radicals preferably contain a total of from 5 to 20 carbon atoms; very particular preference is given to cyclohexyl and menthyl.

Also suitable are linear arylalkyl groups in each case having from 1 to 6 carbon atoms in the alkyl radical and from 6 to 14 carbon atoms in the aryl radical, for example benzyl.

Suitable aryl radicals are aromatic systems having from 6 to 20 carbon atoms in substituted and unsubstituted form, for example phenyl, tolyl, xylyl, p-trifluoromethylphenyl or anisyl; preference is given to using phenyl or o-methoxyphenyl.

Suitable heteroaryl radicals are generally $C_3$–$C_{20}$-compounds which preferably having from 1 to 3 nitrogen atoms per ring, for example pyridyl, pyrimidyl, pyrazinyl or triazinyl, and also heteroaryl bearing alkyl or aryl groups.

The radicals $R^1$ to $R^4$ can also contain atoms from groups IVA, VA, VIA or VIIA of the periodic table of the elements, for example halogen, oxygen, sulfur, nitrogen, silicon, here for example the bis(trimethylsilyl)methyl group. Functional groups such as hydroxyl, alkoxy, amino and cyano which are inert under the polymerization conditions are also possible in this context.

Preferred heterosubstituents $R^1$ to $R^4$ are $C_3$–$C_{30}$-organosilicon radicals, i.e. tetravalent silicon atoms which are attached to $E^1$ or $E^2$ and whose remaining valencies bear three organocarbon radicals, the total number of carbon atoms in these three radicals attached to silicon being in the range from three to thirty. Examples are the trimethylsilyl, t-butyldimethylsilyl or triphenylsilyl group, in particular the trimethylsilyl group.

The radicals $R^1$ to $R^4$ should preferably be sufficiently space-filling for the central atom, e.g. the palladium atom with which the atoms $E^1$ and $E^2$ form the active complex, to be substantially shielded. Radicals which meet this requirement are, for example, cycloaliphatic radicals and also branched aliphatic radicals, particularly those which are branched in the α-position.

The radicals $R^1$ to $R^4$ in a metal complex compound (I) can be identical, identical only in pairs or completely different from one another, i.e. $R^1 \neq R^2 \neq R^3 \neq R^4$. In one embodiment, the radicals $R^1$ and $R^2$ on $E^1$ and $R^3$ and $R^4$ on $E^2$, respectively, are the same, but $R^1$, $R^2$ are not identical with $R^3$, $R^4$.

Suitable electron-withdrawing substituents $R^5$ are linear or branched $C_1$–$C_{20}$-alkyl groups substituted by at least one electron-withdrawing group located in the α-, β-, γ- and/or δ-position, in particular in the α- and/or β-position, relative to Z; $C_6$–$C_{14}$-aryl units substituted by at least one electron-withdrawing group and also nitrile, sulfinyl (—$SO_2R^9$), sulfonyl (—$SO_3R^9$) and nitro groups. The radical $R^9$ can be $C_1$–$C_{20}$-alkyl, in particular $C_1$–$C_{10}$-alkyl such as methyl, ethyl or isopropyl, or $C_6$–$C_{14}$-aryl, in particular phenyl. Furthermore, $R^5$ can be a radical —$C(O)R^{10}$, where $R^{10}$ is linear or branched $C_1$–$C_{20}$-alkyl, $C_6$–$C_{14}$-aryl or aralkyl having from 1 to 10 carbon atoms in the alkyl moiety and from 6 to 14 carbon atoms in the aryl moiety, linear or branched $C_1$–$C_{20}$-alkyl substituted by at least one electron-withdrawing group located in the α-, β-, γ- and/or δ-position relative to the C(O) group, and also $C_6$–$C_{14}$-aryl substituted by at least one electron-withdrawing group.

Possible electron-withdrawing substituents on an alkyl or aryl radical $R^5$ are halogen atoms such as fluorine, chlorine or bromine, preferably fluorine and chlorine and particularly preferably fluorine. The alkyl and aryl radicals may be partially or completely halogenated. Further suitable substituents for the alkyl and aryl radicals are the nitro, nitrile, ester, amide sulfonyl, sulfonylamide and sulfonyl group. The aryl radicals may be substituted by trifluoromethyl or trichloromethyl groups and by ammonium radicals. Examples of suitable alkyl radicals $R^5$ are: trifluoromethyl, trichloromethyl, difluoromethyl, 2,2,2-trifluoroethyl, 2,2,2-trichloroethyl, 3,3,3-trifluoropropyl, pentafluoroethyl, nitromethyl, 2-nitroethyl and cyanomethyl. Preference is given to trifluoromethyl and 2,2,2-trifluoroethyl. Examples of suitable aryl radicals $R^5$ are:

p-, m-, o-fluorophenyl, p-, m-, o-chlorophenyl, 2,4-difluorophenyl, 2,4-dichlorophenyl, 2,4,6-trifluorophenyl, 2,4,6-dichlorophenyl, nitrophenyl, 2,4-dinitrophenyl, 2-chloro-5-nitrophenyl, 2-bromo-5-nitrophenyl, methylsulfinylphenyl and methylsulfonylphenyl.

Further suitable electron-withdrawing radicals $R^5$ are —C(O)$R^{10}$ radicals, where $R^{10}$ may be $C_1$–$C_{20}$-alkyl, $C_6$–$C_{14}$-aryl or $C_1$–$C_{20}$-alkyl and $C_6$–$C_{14}$-aryl substituted by electron-withdrawing groups as described previously for $R^5$. Preferred radicals $R^{10}$ include methyl, ethyl, isopropyl, phenyl, trifluoromethylphenyl, trifluoromethyl or pentafluoroethyl.

$R^5$ is preferably an at least disubstituted phenyl radical such as 2,4-difluorophenyl or 2,4-dichlorophenyl or partially or completely fluorinated alkyl radical with at least two fluorine atoms in the α- or β-position relative to Z, such as trifluoromethyl or 2,2,2-trifluoroethyl.

Suitable formally charged inorganic ligands $L^1$, $L^2$ are hydride, halides, sulfates, phosphates or nitrates. Further suitable ligands $L^1$, $L^2$ are carboxylates or salts of organic sulfonic acids such as methylsulfonate, trifluoromethylsulfonate or p-toluenesulfonate. Of the salts of organic sulfonic acids, preference is given to p-toluenesulfonate. Preferred formally charged ligands $L^1$, $L^2$ are carboxylates, preferably $C_1$–$C_{20}$-carboxylates and especially $C_1$–$C_7$-carboxylates, i.e. for example acetate, trifluoroacetate, propionate, oxalate, citrate or benzoate, with particular preference being given to acetate.

Further suitable formally charged organic ligands $L^1$, $L^2$ are $C_1$–$C_{20}$-aliphatic radicals, $C_3$–$C_{30}$-cycloaliphatic radicals, $C_7$–$C_{20}$-aralkyl radicals having $C_6$–$C_{14}$-aryl radicals and $C_1$–$C_6$-alkyl radicals and also $C_6$–$C_{20}$-aromatic radicals, for example methyl, ethyl, propyl, isopropyl, t-butyl, n-pentyl, isopentyl, cyclohexyl, benzyl, phenyl and aliphatically or aromatically substituted phenyl radicals.

In principle, the ligands $L^1$ and $L^2$ can be present in any ligand combination, i.e. the metal complex (I) can contain, one nitrate radical and one acetate radical, one p-toluenesulfonate radical and one acetate radical, or one nitrate radical and one formally charged organic ligand such as t-butyl. The ligands $L^1$ and $L^2$ in the metal complexes are preferably identical. Of the metal complexes of the formula (I), preference is given to those in which:

M is palladium, $E^1$, $E^2$ are each phosphorus,

Z is nitrogen, $R^1$ to $R^4$ are cycloaliphatic radicals such as cyclohexyl or menthyl, branched aliphatic radicals such isopropyl, s-butyl or t-butyl, aromatic radicals such as phenyl, o-methoxyphenyl or p-trifluoromethylphenyl and heteroaromatic radicals such as pyridyl, particularly preferably phenyl, o-methoxyphenyl and t-butyl, $R^5$ is linear or branched $C_1$–$C_{20}$-alkyl substituted by at least one, preferably at least two electron-withdrawing groups located in the α-, β-, γ- and/or δ-position relative to Z, $C_6$–$C_{14}$-aryl substituted by at least one, preferably at least two, electron-withdrawing groups, —CN, —SO$_2R^9$, —SO$_3R^9$ or —NO$_2$, where $R^9$ is $C_1$–$C_{10}$-alkyl or $C_6$–$C_{14}$-aryl, —C(O)$R^{10}$, where $R^{10}$ is linear or branched $C_1$–$C_{20}$-alkyl, $C_6$–$C_{14}$-aryl or aralkyl having from 1 to 10 carbon atoms in the alkyl moiety and from 6 to 14 carbon atoms in the aryl moiety, linear or branched $C_1$–$C_{20}$-alkyl substituted by at least one electron-withdrawing group located in the α-, β-, γ- and/or δ-position relative to the C(O) group, $C_6$–$C_{14}$-aryl substituted by at least one electron-withdrawing group, A', B' are methylene or ethylene in substituted and unsubstituted form, for example ethylidene or propylidene, benzylidene, o-phenylene, in particular methylene, and $L^1$, $L^2$ are sulfates, phosphates, nitrates, acetate, trifluoroacetate or tosylate, in particular acetate.

Examples of particularly preferred metal complexes include bis(diphenylphosphinomethyl)(2,4-difluorophenyl) amine-palladium bisacetate and bis (diphenylphosphinomethyl)(2,2,2-trifluoroethyl)amine-palladium bisacetate.

The chelating ligands (II) can be used for preparing the metal complexes (I) of the present invention.

The preparation of the chelating ligands (II) can be carried out as described in A. L. Balch, M. M. Olmstead, S. P. Rowley, Inorg. Chim. Acta, 168 (1990), 255–264 or J. Fawcett, P. A. T. Hoye, R. D. W. Kemmitt, D. J. Law, D. R. Russell, J. Chem. Soc., Dalton Trans. 1993, 2563–2568. For example, diphenylphosphine is reacted with paraformaldehyde and 2,4-difluorophenylamine in toluene at 65° C. to give, after a rection time of about 4 h, the chelating phosphine in high yield.

The metal complexes of the present invention having the formula (I) can be prepared by the following methods.

The neutral metal complexes (I) are prepared by replacement of weakly coordinating ligands such as 1,5-cyclooctadiene, benzonitrile or tetramethylethylenediamine which are bound to the corresponding transition metal compounds, for example transition metal carboxylates or transition metal-diorganyls, by the chelating ligands of the general formula (II) as defined above.

The reaction is generally carried out in a solvent such as dichloromethane at from −78 to +40° C.

Furthermore, neutral metal complexes (I) in which $L^1$ and $L^2$ are carboxylate, e.g. acetate, can be prepared by reacting, for example, Pd(OAc)$_2$ with the chelating ligands (II) described in toluene or acetone at room temperature.

A further possible synthetic method is the reaction of the chelate complexes of the general formula (I) with organometallic compounds of groups IA, IIA, IVA and IIB, for example $C_1-C_6$-alkyls of the metals lithium, aluminum, magnesium, tin and zinc, where formally charged inorganic ligands $L^1$, $L^2$ as defined above are replaced by formally charged aliphatic, cycloaliphatic or aromatic ligands $L^1$, $L^2$ likewise as defined above. The reaction is generally carried out in a solvent such as diethyl ether or tetrahydrofuran at from −78 to 65° C.

The metal complexes (I) of the present invention can be used as essential constituent of catalyst systems for preparing copolymers of carbon monoxide and olefinically unsaturated compounds.

Suitable catalyst systems comprise, as active constituents, a) a metal complex (I) as defined above and b) one or more Lewis acids or protic acids or a mixture of Lewis acids and/or protic acids.

The ratio of the catalyst constituents to each other is generally selected such that the molar ratio of metal complex (I) (constituent a)) to Lewis acid and/or protic acid (constituent b)) is in the range from 0.01:1 to 10:1, preferably in the range from 0.1:1 to 1:1.

The constituent a) may be either the exclusive metal complex (I) or a mixture consisting of the defined metal complex (I) and a proportion of free chelating compound (II). If further chelating compound is added, the molar ratio of metal complex (I) to chelating ligand (II) is usually in the range from 0.01:1 to 10:1, preferably in the range from 0.05:1 to 2:1.

The catalyst systems of the present invention can be used for preparing copolymers of carbon monoxide and olefinically unsaturated monomer compounds. The monomers are generally incorporated in the copolymer in alternating order.

Suitable olefinically unsaturated monomer compounds are in principle all monomers of this class of compounds. Preference is given to ethylene and $C_3-C_{20}$-alk-1-enes such as especially propene. It is also possible to use dienes such as 1,4-pentadiene and also cycloolefins such as cyclopentene, cyclohexene, norbornene and norbornadiene and its derivatives.

Olefinically unsaturated aromatic monomers include, first and foremost, styrene and α-methylstyrene.

Further suitable monomers are acrylic acid and methacrylic acid and also their derivatives, among these particularly the nitriles, the amides and the $C_1-C_6$-alkyl esters, for example ethyl acrylate, n-butyl acrylate, t-butyl acrylate, methyl methacrylate.

Further suitable monomers are vinyl chloride, vinyl acetate, vinyl propionate, maleic anhydride and N-vinylpyrrolidone.

It will be appreciated that it is also possible to use mixtures of different monomers, the mixing ratio generally not being critical.

To prepare copolymers of carbon monoxide and olefinically unsaturated monomer compounds, the monomers can be copolymerized in the presence of the catalyst system described above.

As a further process for the preparation of copolymers of carbon monoxide and olefinically unsaturated compounds, it is possible to react the monomers in the presence of a catalyst whose active material is formed from i) a metal M selected from group VIIIB of the periodic table of the elements which is present in the form of a salt or a complex salt, ii) a chelating ligand of the formula (II)

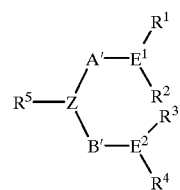

(II)

in which the substituents and indices are as defined above, and iii) one or more protic or Lewis acids or a mixture of protic acids and Lewis acids.

Suitable salts of usually divalent metals M are halides, sulfates, phosphates, nitrates and carboxylates, such as acetates, propionates, oxalates, citrates, benzoates, and also sulfonic acid salts such as methylsulfonates, trifluoromethylsulfonate and p-toluenesulfonate. Preference is given to using carboxylates or sulfonic acid derivatives, especially acetates.

Particularly suitable catalyst components i) are palladium dicarboxylates, preferably palladium diacetate, palladium dipropionate, palladium bis(trifluoroacetate) and palladium oxalate, and also palladium sulfonates, preferably palladium bis(trifluoromethanesulfonate), palladium bis (methanesulfonate), palladium bis(p-toluenesulfonate). Particular preference is given to using palladium diacetate.

Catalyst constituents b) or iii) that can be used are Lewis acids and protic acids and mixtures thereof.

Suitable protic acids b) or iii) are strong mineral acids which preferably have a $pK_a$ of less than 3 such as sulfuric acid, nitric acid, phosphoric acid, tetrafluoroboric acid and perchloric acid, and also strong organic acids, for example trichloroacetic acid and trifluoroacetic acid and also the sulfonic acids, methanesulfonic acid, p-toluenesulfonic acid and benzenesulfonic acid.

The acidic salts of strong acids and weak bases, for example ammonium salts of the abovementioned acids, are also suitable.

Preferred protic acids are sulfuric acids, trifluoroacetic acids and p-toluenesulfonic acid.

Examples of suitable Lewis acids are halides of the elements of group IIIA of the periodic table of the elements, for example boron trifluoride, boron trichloride, aluminum trifluoride, aluminum trichloride, halides of the elements of group VA of the periodic table of the elements, such as phosphorus pentafluoride and antimony pentafluoride, and also halides of the metals of transition group IVB of the periodic table of the elements, for example titanium tetrachloride or zirconium tetrachloride. Further suitable Lewis acids are organically substituted Lewis acids, for example tris(pentafluorophenyl)borane.

Preference is given to using boron trifluoride, antimony pentafluoride or tris(pentafluorophenyl) borane as Lewis acids.

Preferred components b) or iii) are also those which have a weakly coordinating conjugated anion, i.e. an anion which forms only a weak bond with the central metal of the complex, such as tetrafluoroborate, hexafluorophosphate, perchlorate, trifluoroacetate, trifluoromethylsulfonate, p-tosylate and borates, such as catechol borate and tetraaryl borate, particularly suitable aryl groups being 2,5-dimethylphenyl, 2,5-bis(trifluoromethyl)phenyl and pentafluorophenyl.

As component ii), the catalyst systems comprise a chelating compound (II), which has already been described in the discussion of the active constituent a) of the catalyst system of the present invention.

In the in-situ generation of the polymerization catalysts, the metals M are usually used in divalent form as their salts and are brought into contact with the chelating compound ii) of the formula (II) and the acid(s) iii). This can be done before contacting the catalytically active material obtainable in this way with the monomers, generally outside the polymerizaton reactor. However, the reaction of the individual components metal salt i), chelating compound ii) and acid iii) can also be carried out in the polymerization reactor in the presence of the monomers.

The ratio of the catalyst constituents i), ii) and iii) to one another is generally selected such that the molar ratio of the metal compound i) to the component ii) is from 0.01:1 to 10:1, preferably from 0.1:1 to 2:1, and the molar ratio of the metal compound i) to the acid iii) is from 0.01:1 to 100:1, preferably from 0.05:1 to 1:1.

The copolymerization processes for preparing the carbon monoxide copolymers can be carried out either batchwise or continuously.

Reaction parameters which have been found to be suitable for preparing copolymers of carbon monoxide and olefinically unsaturated compounds are pressures from 100 to 500,000 kPa, preferably from 500 to 350,000 kPa and especially from 1000 to 11,000 kPa, and temperatures of from −50 to 400° C., preferably from 10 to 250° C., especially from 40 to 120° C. The copolymerization temperature can easily be maintained in the range from 80 to 120° C. over a period of several hours or more.

The polymerization reactions can be carried out in the gas phase in a fluidized bed or stirred, in suspension, in liquid or supercritical monomers and in solvents which are inert under the polymerization conditions.

Suitable solvents or suspension media for the process according to the invention are, in particular, those which are protic or comprise a proportion of a protic component. For example, low molecular weight alcohols such as methanol, ethanol, i-propanol, n-propanol or water can be used, with preference being given to using methanol as solvent/suspension medium or solvent/suspension medium component.

The polymerization reactions can also be carried out in a virtually alcohol-free or water-free polymerization medium. This means that no further alcohol or water is present in the reaction mixture of monomers, catalyst and possibly inert solvent or suspension medium.

Suitable inert solvents and suspension media are those which contain no hydroxyl group in the molecule, i.e. ethers such as diethyl ether, tetrahydrofuran, aromatic solvents such as benzene, toluene, ethylbenzene, chlorobenzene, aliphatic hydrocarbons such as i-butane or chlorinated aliphatic hydrocarbons such as dichloromethane, 1,1,1-trichloromethane or mixtures of these.

In a polymerization method which has been found to be particularly suitable, the catalyst is placed in an inert solvent, the monomers are subsequently added and the polymerization is carried out at from 40 to 120° C. and at from 1000 to 11,000 kPa. It is also possible to add the metal complex (I), preferably dissolved in an alcoholic solvent such as methanol or a ketone solvent such as acetone, to the monomers and the acid under the reaction conditions.

It has also been found to be particularly suitable to carry out the copolymerization in suspension in the presence of an alcoholic suspension medium, in particular methanol, by adding the monomers to the metal complex (I), in particular palladium acetate, and a protic acid, in particular p-toluenesulfonic acid or sulfuric acid, and polymerizing at from 40 to 150° C., in particular at from 60 to 130° C., and at from 1000 to 11,000 kPa.

The copolymerization processes described can likewise be carried out in the presence of an oxidizing agent such as benzoquinone or naphthoquinone and/or hydrogen.

In the copolymerization processes described, the metal complexes (I) of the present invention have good catalyst productivities which do not decrease under prolonged polymerization times, even at high polymerization temperatures.

The resulting carbon monoxide copolymers usually have a viscosity number VN in the range from 20 to 300 as measured using a 0.5% strength by weight solution in ortho-dichlorobenzene/phenol (1:1). Typical VN values are in the range from 40 to 200 and also in the range from 50 to 150.

The carbon monoxide copolymers of the present invention can be processed by means of injection molding, extrusion, blow molding or spin coating. It is also possible to coat metallic, ceramic and other surfaces, e.g. those of plastic materials.

The carbon monoxide copolymers of the present invention are suitable for the preparation of fibers, sheets, moldings and coatings.

The catalyst systems of the present invention on the basis of metal complexes (I) provide easy access to numerous slightly modified catalysts for the copolymerization of carbon monoxide and olefinically unsaturated compounds. Furthermore, halogen-free starting compounds are used which are easy to handle and readily obtainable, i.e. low-cost, so that even extensive catalyst screening becomes possible.

EXAMPLES

Die $^{31}$p NMR measurements were carried out on a Bruker DPX-250 spectrometer using 85% strength phosphoric acid as an external standard.

Abbreviations:

Pd(OAc)$_2$: Palladium diacetate

Example 1

Bis(diphenylphosphinomethyl)(2,2,2-trifluoroethyl)-amine

Paraformaldehyde (7.5 g) was suspended in toluene (500 ml) and admixed with 2,2,2-trifluoroethylamine (10 g) at 65° C. The reaction mixture was stirred at 65° C. for 20 min, admixed with diphenylphosphine (46.6 g) and refluxed for 5 h. The solvent was then removed under reduced pressure and the residue was dissolved in dichloromethane. The product was precipitated by addition of ethanol, possibly with refrigeration, and filtered off. Drying under reduced pressure gave a white solid (24.3 g yield); $^{31}$P NMR: δ=−27.2 ppm.

Example 2

Bis(diphenylphosphinomethyl)(2,4-difluorophenyl)amine

Paraformaldehyde (1.73 g) was suspended in toluene (500 ml) and admixed with 2,4-difluorophenylamine (3.6 g) at 65° C. The reaction mixture was stirred at 65° C. for 20 min, admixed with diphenylphosphine (10 ml) and refluxed for 5 h. The solvent was then removed under reduced pressure and the residue was dissolved in dichloromethane. The product was precipitated by addition of ethanol, possibly with refrigeration, and filtered off. Drying under reduced pressure gave a white solid (9.83 g yield); $^{31}$P NMR: δ=−26.3 ppm.

B. Preparation of defined Pd(OAc)$_2$ complexes (I)

a) Bis(diphenylphosphinomethyl)(2,2,2-trifluoroethyl) amine-palladium bisacetate Pd(OAc)$_2$ (0.45 g) was dissolved in 50 ml of degassed acetone, stirred at room temperature for 2 h and then filtered. The resulting solution was admixed with bis (diphenylphosphinomethyl)(2,2,2-trifluoroethyl)amine (1.1 g), dissolved in 50 ml of degassed acetone. The solution was stirred for half an hour, reduced to a volume of 10 ml and admixed with 100 ml of diethyl ether, whereupon crystals began to form. The crystallization was supported by cooling with ice. The resulting palladium chelate complex was filtered off, washed with toluene and dried under reduced pressure (0.62 g yield); $^{31}$P NMR: δ=8.6 ppm.

b) Bis(diphenylphosphinomethyl)(2,4-difluorophenyl) amine-palladium bisacetate

Pd(OAc)$_2$ (0.45 g) was dissolved in 50 ml of degassed acetone, stirred at room temperature for 2 h and then filtered. The resulting solution was admixed with bis (diphenylphosphinomethyl)(2,4-difluorophenyl)amine (1.16 g) dissolved in 50 ml of degassed acetone. The solution was stirred for half an hour, reduced to a volume of 10 ml and admixed with 100 ml of diethyl ether, whereupon crystals began to form. The crystallization was supported by cooling with ice. The resulting palladium chelate complex was filtered off, washed with toluene and dried under reduced pressure (1.0 g yield); $^{31}$P NMR: δ=9.0 ppm.

C. Colymerization procedures a) Copolymerization of carbon monoxide and ethene in a 0.3 l autoclave A 0.3 l autoclave was charged with 100 g of methanol, bis(diphenylphosphinomethyl)(2,4-difluorophenyl)amine-palladium bisacetate (19 mg) and p-toluenesulfonic acid (17 mg). The system was pressurized to an initial pressure of 30 bar using an ethene/carbon monoxide mixture (1:1), heated to 85° C. and pressurized with ethene/CO until a pressure of 60 bar was obtained. The temperature and the partial pressures of the monomers were kept constant over the whole reaction time. After five hours at the abovementioned conditions, the polymerization was terminated by cooling and venting the autoclave. The product mixture was filtered off and the residue was dried under reduced pressure. Yield: 45 g. Catalyst activity=16.6 kg (carbon monoxide copolymer/g(palladium)/h.

b) Terpolymerization of carbon monoxide, ethene and propene in a 3.5 l autoclave A 3.5 l autoclave was charged with methanol (1.0 l), propene (100 g) and p-toluenesulfonic acid (0.175 mmol). The system was then heated to a reaction temperature of 90° C. and pressurized to 80 bar using carbon monoxide/ethene (1:1). Bis(diphenylphosphinomethyl)(2,2, 2-trifluoroethyl)amine-palladium bisacetate (0.05 mmol) dissolved in 50 ml of methanol were added under these reaction conditions. The temperature and the pressure were kept constant over the whole reaction time. After a reaction of 5 h, the polymerization was terminated by cooling and venting the autoclave. The product mixture was filtered and the residue dried under reduced pressure. Yield: 371 g. Catalyst activity=13.95 kg (carbon monoxide copolymer)/g (palladium)/h.

c) Terpolymerization of carbon monoxide, ethene and propene in a 9 l autoclave

A 9 l autoclave was charged with methanol (4.0 l), propene (400 g) and p-toluenesulfonic acid (0.7 mmol). The system was then heated to a reaction temperature of 90° C.

and pressurized to 100 bar using carbon monoxide/ethene (1:1). Bis(diphenylphosphinomethyl)(2,2,2-trifluoroethyl) amine-palladium bisacetate (0.05 mmol) dissolved in 50 ml of methanol were added under these reaction conditions. The temperature and the pressure were kept constant over the whole reaction time. After a reaction time of 6 h, the polymerization was terminated by cooling and venting the autoclave. The product mixture was filtered and the residue was dried under reduced pressure. Yield: 279 g. Catalyst activity=10.91 kg (carbon monoxide copolymer)/g (palladium)/h.

The recovered carbon monoxide copolymer had a reduced viscosity number VN of 75 ml/g as measured using a 0.5% strength by weight solution in ortho-dichlorobenzene/phenol (1:1).

We claim:

1. A cis-bridged metal complex of the formula (I)

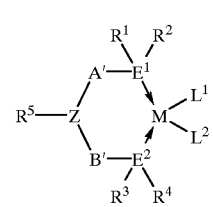

(I)

where:

$R^5$ is an electron-withdrawing radical,

M is a metal of group VIIIB of the periodic table of the elements, $E^1$, $E^2$ are each an element of group VA of the periodic table of the elements, z is nitrogen or phosphorus, $R^1$ to $R^4$ are substituents selected, independently of one another, from the group consisting of $C_1$–$C_{20}$-organocarbon and $C_3$–$C_{30}$-organosilicon radicals in substituted and unsubstituted form, A', B' are $C_1$–$C_4$-alkylene units in substituted or unsubstituted form, silylene-bridged organic radicals or $NR^6$ radicals, $R^6$ is hydrogen or a substituent selected from the group consisting of $C_1$–$C_{20}$-organocarbon and $C_3$–$C_{30}$-organosilicon radicals, and $L^1$,$L^2$ are formally charged ligands.

2. A metal complex as claimed in claim 1, wherein $R^5$ is:

linear or branched $C_1$–$C_{20}$-alkyl substituted with at least one electron-withdrawing group located in the α-, β-, γ- and/or δ-position relative to Z;

$C_6$–$C_{14}$-aryl substituted with at least one electron-withdrawing group or —CN, —SO$_2$R$^9$, —SO$_3$R$^9$ or —NO$_2$, where $R^9$ is $C_1$–$C_{10}$-alkyl or $C_6$–$C_{14}$-aryl;

—C(O)R$^{10}$, where $R^{10}$ is linear or branched $C_1$–$C_{20}$-alkyl, $C_6$–$C_{14}$-aryl, aralkyl having from 1 to 10 carbon atoms in the alkyl moiety and from 6 to 14 carbon atoms in the aryl moiety, linear or branched $C_1$–$C_{20}$-alkyl substituted by at least one electron-withdrawing group located in the α-, β-, γ- and/or δ-position relative to the C(O) group or $C_6$–$C_{14}$-aryl substituted by at least one electron-withdrawing group.

3. A process for the preparation of metal complexes of the formula (I) as claimed in claim 1, which comprises reacting, in a solvent, a metal M selected from group VIIIB of the periodic table of the elements which is present in the form of a salt or a complex salt and carries formally charged ligands $L^1$ and $L^2$ with chelating ligands of the formula (II)

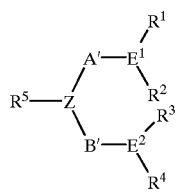

(II)

where:
- $R^5$ is an electron-withdrawing radical,
- $E^1$, $E^2$ are each an element of group VA of the periodic table of the elements,
- z is nitrogen or phosphorus,
- $R^1$ to $R^4$ are substituents selected, independently of one another, from the group consisting of $C_1$–$C_{20}$-organocarbon and $C_3$–$C_{30}$-organosilicon radicals in substituted and unsubstituted form,
- A', B' are $C_1$–$C_4$-alkylene units in substituted or unsubstituted form, silylene-bridged organic radicals or $NR^6$ radicals, and
- $R^6$ is hydrogen or a substituent selected from the group consisting of $C_1$–$C_{20}$-organocarbon and $C_3$–$C_{30}$-organosilicon radicals.

4. A catalyst system comprising, as active constituents,
a) a metal complex of the formula (I) as claimed in claim 1 and
b) one or more Lewis acids or protic acids or a mixture of Lewis acids and protic acids.

5. A process for the preparation of copolymers of carbon monoxide and olefinically unsaturated compounds, which comprises conducting the copolymerization in the presence of a catalyst system as claimed in claim 4.

6. A process for the preparation of copolymers of carbon monoxide and olefinically unsaturated monomer compounds, which comprises polymerizing the monomers in the presence of
i) a metal M selected from group VIIIB of the periodic table of the elements which is present in the form of a salt or a complex salt,
ii) a chelating ligand of the formula (II)

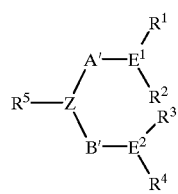

(II)

where:
- $R^5$ is an electron-withdrawing radical,
- $E^1$, $E^2$ are each an element of group VA of the periodic table of the elements,
- z is nitrogen or phosphorus,
- $R^1$ to $R^4$ are substituents selected, independently of one another, from the group consisting of $C_1$–$C_{20}$-organocarbon and $C_3$–$C_{30}$-organosilicon radicals in substituted and unsubstituted form,
- A', B' are $C_1$–$C_4$-alkylene units in substituted or unsubstituted form, silylene-bridged organic radicals or $NR^6$ radicals,
- $R^6$ is hydrogen or a substituent selected from the group consisting of $C_1$–$C_{20}$-organocarbon and $C_3$–$C_{30}$-organosilicon radicals, and iii) one or more protic acids or Lewis acids or a mixture of protic acids and Lewis acids.

7. A fiber, sheet, molding or coating comprising a copolymer produced by the process of claim 5.

8. A process for the preparation of copolymers of carbon monoxide and olefinically unsaturated compounds, which comprises conducting the copolymerization in the presence of a catalyst system having the metal complex as claimed in claim 1 as an essential constituent.

* * * * *